US007700365B2

(12) United States Patent
Singh et al.

(10) Patent No.: US 7,700,365 B2
(45) Date of Patent: Apr. 20, 2010

(54) VITAMIN D DEFICIENCIES

(75) Inventors: Ravinder J. Singh, Rochester, MN (US); Robert L. Taylor, Rochester, MN (US); Stefan Grebe, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1249 days.

(21) Appl. No.: 10/977,121

(22) Filed: Oct. 29, 2004

(65) Prior Publication Data

US 2006/0094125 A1     May 4, 2006

(51) Int. Cl.
*G01N 23/00* (2006.01)
(52) U.S. Cl. ....................... 436/140; 436/173
(58) Field of Classification Search .......... 436/140, 436/173
See application file for complete search history.

(56) References Cited

U.S. PATENT DOCUMENTS

| 6,692,971 | B2 | 2/2004 | Shushan et al. | |
|---|---|---|---|---|
| 2006/0228808 | A1 | 10/2006 | Clarke et al. | 436/173 |
| 2006/0228809 | A1 | 10/2006 | Clarke et al. | 436/173 |

OTHER PUBLICATIONS

Jones and Makin, "Chapter 4. Electrospray (ESI) and Atmospheric Pressure Chemical Ionization (APCI)" in the book of Leenheer et al. "Modern Chromatographic Analysis of Vitamins", CRS Press. Published 2000, p. 216.*
Gong, et al., "Routine simultaneous measurement of 25-hydroxyvitamin D2 and D3 by isotope-dilution liquid chromatography—tandem mass spectrometry assay," Clinical Biochemistry 41, (2008), p. 1268.*
Singh, R., et al, "C-3 Epimers Can Account for a Significant Proportion of Total Circulating 25-Hydroxyvitamin D in Infants, Complicating Accurate Measurement and Interpretation of Vitamin D Status" The Journal of Clinical Endocrinology & Metabolism, vol. 91(8); pp. 3055-3061, (2006).
Tsugara et al., "Determination of 25-Hydroxyvitamin D in Human Plasma Using High-Performance Liquid Chromatography-Tandem Mass Spectrometry," Anal. Chem., 2005, 77:3001-3007.
Maunsell et al., "Routine Isotope-Dilution Liquid Chromatography-Tandem Mass Spectrometry Assay for Simultaneous Measurement of the 25-Hydroxy Metabolites of Viramins $D_2$ and $D_3$," Clin. Chem, 2005, 51(9):1683-1690.

Yeung et al., "Characterization of vitamin $D_3$ metabolites using continuous-flow fast atom bombardment tandem mass spectrometry and high-performance liquid chromatography," *J. Chromatography*, 1993, 645:115-123.
Busch, "A Glossary for Mass Spectrometry," *Mass Spectrometry*, 2002, 17(6S):S26-S34.
Coldwell et al., "Stable isotope-labeled vitamin D, metabolites and chemical analogs: synthesis and use in mass spectrometric studies," *Steroids*, 1990, 55(10):418-432.
Higashi et al., "Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent," *Biol. Pharm. Bull.*, 2001, 24(7):738-743.
Jones et al., "Current understanding of the molecular actions of Vitamin D," *Physiological Reviews*, 1998, 78:1193-1231.
Miller and Portale, "Genetic causes of rickets," *Current Opinion in Pediatrics*, 1999, 11:333-339.
"PE SCIEX API 365" [online]. University Children's Hospital Zurich, [retrieved on Oct. 26, 2004]. Retrieved from the Internet: <URL: www.kispi.unizh.ch/clindhem/ms/instruments/sciex_.html>.
Vieth et al., Age-related changes in the 25-hydroxyvitamin D versus parathyroid hormone relationship suggest a different reason why older adults require more vitamin D, *J. Clin. Endocrin. Metabol.*, 2003, 88:185-191.
Vieth, "Vitamin D supplementation, 25-ydroxyvitamin D concentrations, and safety," *Am. J. Clin. Nutr.*, 1999, 69(5):842:856.
Vogeser et al., "Candidate Reference Method for the Quantification of Circulating 25-Hydroxyvitamin D3 by Liquid Chromatography-Tandem Mass Spectrometry," *Clin. Chem.*, 2004, 50(8):1415-1417.
Watson et al., "Analysis of vitamin D and its metabolites using thermospray liquid chromatography/mass spectrometry," *Biomed. Chromatogr.*, 1991,5(4):153-160.
Wharton and Bishop, "Rickets," *Lancet*, 2003, 362:1389-1400.
Bartolucci et al., "Liquid chromatography tandem mass spectrometric quantitation of sulfamethazine and its metabolites: direct analysis of swine urine by triple quadrupole and by ion trap mass spectrometry," *Rapid Comm. In Mass Spectrometry*, 14, 967-973 (2000).
Holick et al., "Evaluation of Precision and Accuracy of Nichols Advantage 25-Hydroxyvitamin D Assay for 25-Hydroxyvitamin $D_2$ and 25-Hydroxyvitamin $D_3$: Comparison to Four Other Assay Methods Including Liquid Chromatography-Mass Spectrometry," *26th Annual Meeting of the American Society for Bone and Mineral Research*, Abstract No. SU585, Oct. 1-5, 2004.

* cited by examiner

*Primary Examiner*—Jill Warden
(74) *Attorney, Agent, or Firm*—Fish & Richardson P.C.

(57) ABSTRACT

Methods for determining the amount of vitamin D compounds in a sample are provided. The methods can employ LC-MS/MS techniques and optionally the use of deuterated internal standards. Methods for diagnosing vitamin D deficiencies are also provided.

12 Claims, 3 Drawing Sheets

VITAMIN D DEFICIENCIES

TECHNICAL FIELD

This document relates to methods and materials for detecting vitamin D compounds (e.g., 25-hydroxyvitamin D2 and 25-hydroxyvitamin D3) in a sample.

BACKGROUND

Vitamin D compounds are derived from dietary ergocalciferol (from plants, vitamin D2) or cholecalciferol (from animals, vitamin D3), or by conversion of 7-dihydrocholesterol to vitamin D3 in the skin upon UV-exposure. Vitamin D2 and D3 are subsequently 25-hydroxylated in the liver to form 25-hydroxyvitamin D2 (25OHD2) and 25-hydroxyvitamin D3 (25OHD3). 25OHD2 and 25OHD3 represent the main body reservoir and transport form of vitamin D; they are stored in adipose tissue or are tightly bound by a transport protein while in circulation.

The exact levels of 25OHD2 and 25OHD3 that reflect optimal body stores are uncertain. Mild to modest deficiency can be associated with osteoporosis or secondary hyperparathyroidism. Severe deficiency may lead to failure to mineralize newly formed osteoid in bone, resulting in rickets in children and osteomalacia in adults.

Current immunoassay-based analytical methods for detecting 25OHD2 and 25OHD3 cannot selectively differentiate between 25OHD2 and 25OHD3 and can under-detect the amount of 25-OHD2. HPLC methods can use labor intensive extraction processes followed by long chromatographic run times.

SUMMARY

This document provides materials and methods that can be used to measure 25OHD2 and 25OHD3 levels in a sample. For example, 25OHD2 and 25OHD3 can be selectively detected and quantitated using mass spectrometric techniques. The materials and methods are useful to aid in the diagnosis of vitamin D deficiencies or hypervitaminosis D, and to monitor vitamin D replacement therapies. In one embodiment, this document provides a LC-MS/MS method employing on-line sample extraction to allow for the sensitive, accurate, and precise quantification of 25OHD2, 25OHD3, or both, in samples such as serum and plasma. Unlike manual immunoassays, the methods provided herein can be highly automated, can separately measure 25OHD2 and 25OHD3, and can use an internal standard to monitor recovery of the sample extraction process. In addition, the methods can provide superior analytical performance as compared to immunoassays.

In general, one embodiment provides a method for determining an amount of 25-hydroxyvitamin D2 in a sample. The method includes using a mass spectrometry technique to determine the amount of 25-hydroxyvitamin D2. The MS technique can employ atmospheric pressure chemical ionization. The mass spectrometry technique can be a tandem mass spectrometry (MS/MS) technique, or a LC-MS/MS technique. The LC can include an on-line extraction of the sample. The LC-MS/MS technique can include the use of a triple quadrupole instrument in Multiple Reaction Monitoring (MRM), positive-ion mode, and can include a Q1 scan tuned to select a precursor ion that corresponds to the [M+H$^+$]s of 25-hydroxyvitamin D$_2$.

In another embodiment, the amount of 25-hydroxyvitamin D3 can also be determined in addition to the amount of 25-hydroxyvitamin D2. In this embodiment, an LC-MS/MS technique can include a Q1 scan tuned to select, independently, precursor ions that correspond to the [M+H$^+$] of 25-hydroxyvitamin D$_2$ and 25-hydroxyvitamin D$_3$. An LC-MS/MS technique can include monitoring MRM precursor-product ion pair transitions having m/z values of 401.4/383.3 for 25-hydroxyvitamin D$_3$ and 413.0/395.3 for 25-hydroxyvitamin D$_2$.

An internal standard, such as a deuterated 25-hydroxyvitamin D2 or D3, can be employed in any of the methods described herein. In certain cases, the internal standard is d$_6$-25-hydroxyvitamin D$_3$ having a MRM parent-daughter ion pair transition m/z value of 407.4/389.5.

A sample can be a biological or non-biological sample. A sample can be a human biological sample, such as a blood, urine, lachrymal, plasma, serum, or saliva sample.

In another embodiment, a method for determining whether or not a mammal has a vitamin D deficiency is provided. The method includes determining the amount of 25-hydroxyvitamin D2 and 25-hydroxyvitamin D3 in a sample from the mammal. Any of the methods described herein can be used to determine these amounts. A total amount of 25-hydroxyvitamin D2 and 25-hydroxyvitamin D3 of <25 ng/mL indicates that the mammal has the vitamin D deficiency.

In yet another embodiment, a method for determining whether or not a mammal has hypervitaminosis D is provided. The method includes determining the amount of 25-hydroxyvitamin D2 and 25-hydroxyvitamin D3 in a sample from the mammal, where a total amount of 25-hydroxyvitamin D2 and 25-hydroxyvitamin D3 of >80 ng/mL indicates the mammal has hypervitaminosis D.

A method for monitoring vitamin D replacement therapy in a mammal is also provided. The method includes determining the amount of 25-hydroxyvitamin D2 in a sample from the mammal using one of the methods described herein. A lower concentration of 25-hydroxyvitamin D$_2$ relative to the vitamin D replacement therapy is indicative of one or more of the following: non-compliance with the replacement therapy, malabsorption of vitamin D supplements, and resistance to 25-hydroxyvitamin D2.

Other features and advantages of the invention will be apparent from the following detailed description, and from the claims. Unless otherwise defined, all technical and scientific terms used herein have the meaning commonly understood by one of ordinary skill in the art to which this invention pertains. All publications, patent applications, patents, and other references mentioned herein are incorporated by reference in their entirety. In case of conflict, the present specification, including definitions, will control. The disclosed materials, methods, and examples are illustrative only and not intended to be limiting. Skilled artisans will appreciate that methods and materials similar or equivalent to those described herein can be used to practice the invention.

DETAILED DESCRIPTION

Figure 1:
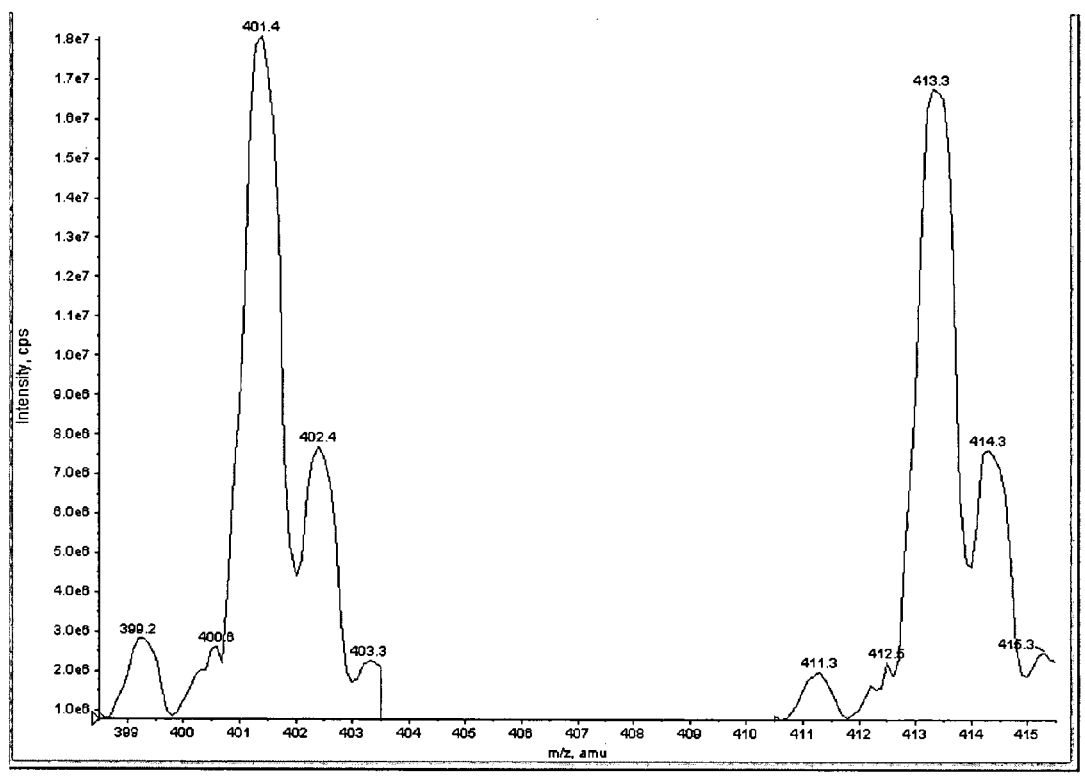
FIG. 1 is a Q1 scan of 25OHD2 and 25OHD3.

Materials and methods for determining the amount of 25OHD2 and/or 25OHD3 in a sample, such as a sample from a patient in a clinical setting, are provided. The methods can be highly automated to allow for the efficient analysis of a number of samples in minimal time. In addition, the methods can be highly sensitive and can allow for the accurate differentiation of 25OHD2 and 25OHD3, thus avoiding the underdetection of one or both of the analytes by other methods. On-line extraction methods can be employed, further minimizing sample handling and optimizing run time.

A method described herein can include the use of mass spectrometry techniques, such as tandem mass spectrometry (MS/MS) techniques. In certain cases, a liquid chromatography tandem mass spectrometry (LS-MS/MS) technique can be used. A mass spectrometry technique can include the use of a triple quadrupole instrument in Multiple Reaction Monitoring, positive ion mode. Depending on the analyte of interest, a MS/MS technique can include a Q1 scan that is tuned to select precursor ions that correspond to the positive ions ([M+H+]) of 25OHD2 and/or 25OHD3. Precursor-product ion pairs transitions characteristic for 25OHD2 and/or 25OHD3 can be monitored. An internal standard, such as deuterated 25OHD3, can be added to any sample, e.g., to evaluate sample recovery, precision, and/or accuracy.

Samples and Sample Preparation

A sample for analysis can be any sample, including biological and non-biological samples. For example, a sample can be a food (e.g., meat, dairy, or vegetative sample) or beverage sample (e.g., orange juice or milk). A sample can be a nutritional or dietary supplement sample. In certain cases, a sample can be a biological sample, such as a tissue (e.g., adipose, liver, kidney, heart, muscle, bone, or skin tissue) or biological fluid (e.g., blood, serum, plasma, urine, lachrymal fluid, or saliva) sample. The biological sample can be from a mammal. A mammal can be a human, dog, cat, primate, rodent, pig, sheep, cow, or horse.

A sample can be treated to remove components that could interfere with the mass spectrometry technique. A variety of techniques known to those having skill in the art can be used based on the sample type. Solid and/or tissue samples can be ground and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets. A sample can be de-proteinized. For example, a plasma sample can have serum proteins precipitated using conventional reagents such as acetonitrile, KOH, NaOH, or others known to those having ordinary skill in the art, optionally followed by centrifugation of the sample.

In certain cases, an internal standard can be added to a sample prior to sample preparation. Internal standards can be useful to monitor extraction/purification efficiency. For example, 25OHD2 and 25OHD3 can bind to serum proteins such as vitamin D-binding globulin. An internal standard can be added to a sample and allowed to equilibrate for a period of time, e.g., 5, 10, 15, 20, 25, 30, 60, 120 or more minutes. Equilibration temperature can be from about 10° C. to about 45° C., or any value in between (e.g., 15, 25, 30, 35, 37, 42, or 44° C.). In certain cases, equilibration can be at room temperature for about 15 minutes.

An internal standard can be any compound that would be expected to behave under the sample preparation conditions in a manner similar to that of one or more of the analytes of interest. For example, a stable-isotope-labeled version of an analyte of interest can be used, such as a deuterated version of an analyte of interest. While not being bound by any theory, the physicochemical behavior of such stable-isotope-labeled compounds with respect to sample preparation and signal generation would be expected to be identical to that of the unlabeled analyte, but clearly differentiable by mass on the mass spectrometer. In certain methods, deuterated 25OHD2 or deuterated 25OHD3 can be employed. For example, d6-25OHD3 can be used.

To improve run time and minimize hands-on sample preparation, on-line extraction and/or analytical chromatography of a sample can be used. On-line extraction and/or analytical chromatography can be used, e.g., in LC-MS/MS techniques. For example, in certain methods, a sample, such as a deproteinized plasma sample, can be extracted using an extraction column, followed by elution onto an analytical chromatography column. The columns can be useful to remove interfering components as well as reagents used in earlier sample preparation steps (e.g., to remove reagents such as acetonitrile). Systems can be co-ordinated to allow the extraction column to be running while an analytical column is being flushed and/or equilibrated with solvent mobile phase, and vice-versa, thus improving efficiency and run-time. A variety of extraction and analytical columns with appropriate solvent mobile phases and gradients can be chosen by those having ordinary skill in the art. Analytes that elute from an analytical chromatography column can be then measured by mass spectrometry techniques, such as tandem mass spectrometry techniques.

Mass Spectrometry

After sample preparation, a sample can be subjected to a mass spectrometry (MS) technique. A mass spectrometry technique can use atmospheric pressure chemical ionization (APCI) in the positive ion mode to generate precursor positive ions. In APCI techniques, analytes of interest exist as charged species, such as protonated molecular ions [M+H$^+$] in the mobile phase. During the ionization phase, the molecular ions are desorbed into the gas phase at atmospheric pressure and then focused into the mass spectrometer for analysis and detection. Additional information relating to atmospheric pressure chemical ionization is known to those of skill in the art; see U.S. Pat. No. 6,692,971.

MS analysis can be conducted with a single mass analyzer (MS) or a "tandem in space" analyzer such as a triple quadrupole tandem mass spectrometer (MS/MS). Using MS/MS, the first mass filter (Quadrople 1, Q1) can select, or can be tuned to select, independently, one or more of the molecular ions of 25OHD2, 25OHD3, and the internal standard. The second mass filter (Q3) is tuned to select specific product or fragment ions related to the analyte of interest. Between these two mass filtration steps, the precursor molecular ions can undergo collisionally-induced dissociation (CID) at Q2 to produce product or fragment ions. The previously-described mass spectrometry technique can also be referred to as multiple reaction monitoring, or MRM. In multiple reaction monitoring, both quadrupoles Q1 and Q3 can be fixed (or tuned) each at a single mass, whereas Q2 can serve as a collision cell.

The precursor [M+H$^+$] ions of 25OHD2 and 25OHD3 typically produce product ions that reflect the loss of water from the sample. Accordingly, precursor-product ion pair transitions for 25OHD2 can have m/z values of 413.0 and 395.3, while 25OHD3 can have precursor-product ion pair transitions having m/z values of 401.4 and 383.3. Similarly, the internal standard d6-25OHD3 can have precursor-product ion pair transitions having m/z values of 407.4 and 389.5. The amount of each can be determined by comparing the area of precursor or product transitions, or both, of 25OHD2 and/or 25OHD3, with those of a standard calibration curve, e.g., a standard calibration curve generated from a series of defined concentrations of pure 25OHD2 and/or 25OHD3 standards. Variables due to the extraction and the LC-MS/MS instrumentation can be normalized by normalizing peak areas of the analyte of interest to the peak areas of the internal standard.

Any tandem MS machine and LC-MS/MS machine can be used, including the API 4000 triple quadrupole tandem mass spectrometer (ABI-SCIEX, Toronto, Canada). Software for tuning, selecting, and optimizing ion pairs is also available, e.g., Analyst Software Ver. 1.4 (ABI-SCIEX).

Methods for Diagnosis

The methods described herein can be used in various diagnostic applications to monitor vitamin D-related pathologies, vitamin D and calcium homeostasis, and vitamin D replacement therapies. For example, the total amount of 25OHD2 and 25OHD3 in a sample, such as a human patient sample, can be compared with clinical reference values to diagnose a vitamin D deficiency or hypervitaminosis D. One set of clinical reference values is set forth below, and represents clinical decision values that can apply to human males and females of all ages, rather than population-based reference values. Such population-based reference values have been found to vary widely depending on ethnic background, age, geographic location of the studied population, and sampling season, and correlate poorly with concentrations associated with biologically and clinically relevant vitamin D effects.

| Clinical reference values, total 25OHD2 and 25OHD3 | |
| --- | --- |
| <10 ng/mL | Severe deficiency* |
| 10 ng/mL-25 ng/mL | Mild to moderate deficiency** |
| 25 ng/mL-80 ng/mL | Optimum levels*** |
| >80 ng/mL | Toxicity possible |

*Could be associated with ostemalacia or rickets
**May be associated with increased risk of osteoporosis or secondary hyperparathyroidism
***Optimum levels in the normal population
****80 ng/mL is the lowest reported level associated with toxicity in patients without primary hyperparathyroidism who have normal renal function. Most patients with toxicity have levels in excess of 150 ng/mL. Patients with renal failure can have very high 25OHD2 and 25OHD3 levels without any signs of toxicity, as renal conversion to the active hormones is impaired or absent.

In one embodiment, a method for determining whether or not a mammal has a vitamin D deficiency is provided. The method can involve determining the amount of 25OHD2 and 25OHD3 in a sample from the mammal, such as a human. The amounts can be determined using any of the methods provided herein. Based on the clinical reference values set forth herein, a total amount of 25OHD2 and 25OHD3 of less than 25 ng/mL in the sample can indicate that the mammal has a vitamin D deficiency.

In another embodiment, a method for determining whether or not a mammal has hypervitaminosis D is provided. The method can involve determining the amount of 25OHD2 and 25OHD3 in a sample from the mammal. Based on the clinical reference values set forth herein, a total amount of 25OHD2 and 25OHD3 of more than 80 ng/mL in the sample can indicate that the mammal has hypervitaminosis D.

In yet another embodiment, a method for monitoring vitamin D replacement therapy in a patient is provided. The method can involve determining the amount of 25OHD2 in a sample from the patient using any of the methods described herein. A lower than expected concentration of 25OHD2 relative to the amount expected from the replacement therapy can be indicative of patient non-compliance, malabsorption of vitamin D supplements, or resistance to 25OHD2.

EXAMPLES

Example 1

Development of a High-Throughput LC-MS/MS Assay Using on-Line Extraction for the Measurement of 25OHD2 and 25OHD3

Materials

25OHD2 and 25OHD3 were purchased from Sigma (St. Louis, Mo.). Each compound was reconstituted separately in ethanol and analyzed for concentration by UV Spectrophotometry at 264 nm using an ethanol blank. The analytes were combined in a stock solution and stored at −20° C. Working standards were prepared by diluting the stock solution in stripped serum (Sera Care Inc.) with concentrations of 0-200 ng/mL (0-500 nmol/L).

Deuterated $d_6$-25OHD3 was purchased from AS VITAS (Norway) for use as an internal standard. The compound was reconstituted in ethanol and stored at −20° C. A working internal standard solution was created by diluting the stock internal standard in 70% methanol containing 1 µg/mL estriol.

Sample Preparation

25 µL of working internal standard was added to 200 µL sample. The sample was then incubated for 15 minutes at room temperature to allow the internal standard time to equilibrate with any binding proteins in the sample. Proteins were then precipitated by addition of 200 µL of acetonitrile and separated from the supernatant by centrifugation. The supernatant was then transferred to a 96-deep-well plate and covered with a template film until analysis.

On-Line Extraction and LC-MS/MS

On-line extraction and HPLC chromatography of the supernatants was performed using a Cohesive Technologies TX4 Turbo Flow system with 1.0×50 mm Cyclone extraction columns and 3.3 cm×4.6 mm, 3 µm LC-18 (Supelco) analytical columns.

50 µL of the supernatant was injected onto the Cyclone extraction column with a mobile phase of 50% methanol, 0.005% formic acid at 4.0 mL/min for 30 seconds. While the supernatant was injected onto the extraction column, the LC-18 analytical column was equilibrated with 17.5% methanol, 0.005% formic acid at 0.75 mL/min. The analytes were then eluted from the extraction column for 90 seconds with methanol, 0.005% formic acid at 0.2 mL/min, mixed at a T-valve with 17.5% methanol, 0.005% formic acid flowing at 0.55 mL/min to give a mobile phase of 39.5% methanol, 0.005% formic acid, onto the analytical column. There was a step gradient to 87% methanol, 0.005% formic acid for the analytical column, and the analytes were measured by tandem mass spectrometry. The extraction column and analytical column were then equilibrated with original conditions for 1 minute.

Analytes were analyzed on an API 4000 triple-quadrupole tandem mass spectrometer (ABI-SCIEX, Toronto, Canada) using Analyst Software, Ver. 1.4 (ABI-SCIEX). An atmospheric pressure chemical ionization (APCI) source was used at a temperature of 400° C. The MS/MS parameters were curtain gas 10, GS1 22, CAD 6, NC 3, DP, 31, EP, 10, CE 13 and CXP 10. The ion transitions monitored were m/z 401.4/383.3 for 25OHD3, m/z 413.0/395.3 for 25OHD2 and m/z 407.4/389.5 for $d_6$-25OHD3.

Samples

Serum separator (SST), serum-clot, EDTA, and sodium heparin tubes from 5 normal volunteers were collected to assess stability and specimen type. Due to the lack of 25-OH D2 in normal donors samples, specimen-type suitability was established by a recovery study on each sample type. Stability samples were also spiked prior to storage.

Linearity was established by diluting 5 elevated samples from the Diasorin RadioImmunoAssay (RIA) (Stillwater, Minn.) in stripped serum (stripped of endogenous vitamin D). The 25OHD2 and 25OHD3 values obtained from the undiluted sample were used to calculate the expected values of the diluted sample. The percentage of observed/expected was then calculated for each dilution and used as a measure of linearity.

To create quality control pools and establish precision, stripped serum was separated into 3 pools and spiked with 25OHD2 and 25OHD3 to a low, medium and high level. Each pool was separated into 20-mL aliquots and frozen at −80° C. One 20-mL aliquot was thawed, separated into 1.0-mL aliquots and refrozen at −20° C. Inter-assay precision was established by running an aliquot of each pool each day for 15 days. Sensitivity was established by inter-assay precision on a low pool diluted in stripped serum. Intra-assay precision was established by running 20 separate samples on each of 3 levels on the same assay.

A method comparison was done on 100 samples for the LC-MS/MS method, the Diasorin RIA, the ADVANTAGE automated chemiluminescent immunoassay (Nichols Diagnostics), and the LIASON automated chemiluminescent immunoassay (Diasorin, Stillwater, Minn.). The samples were separated into 5 aliquots and frozen at −20° C. An aliquot was used for each method.

LC-MS/MS Characteristics of 25OHD2 and 25OHD3

Figure 2A:
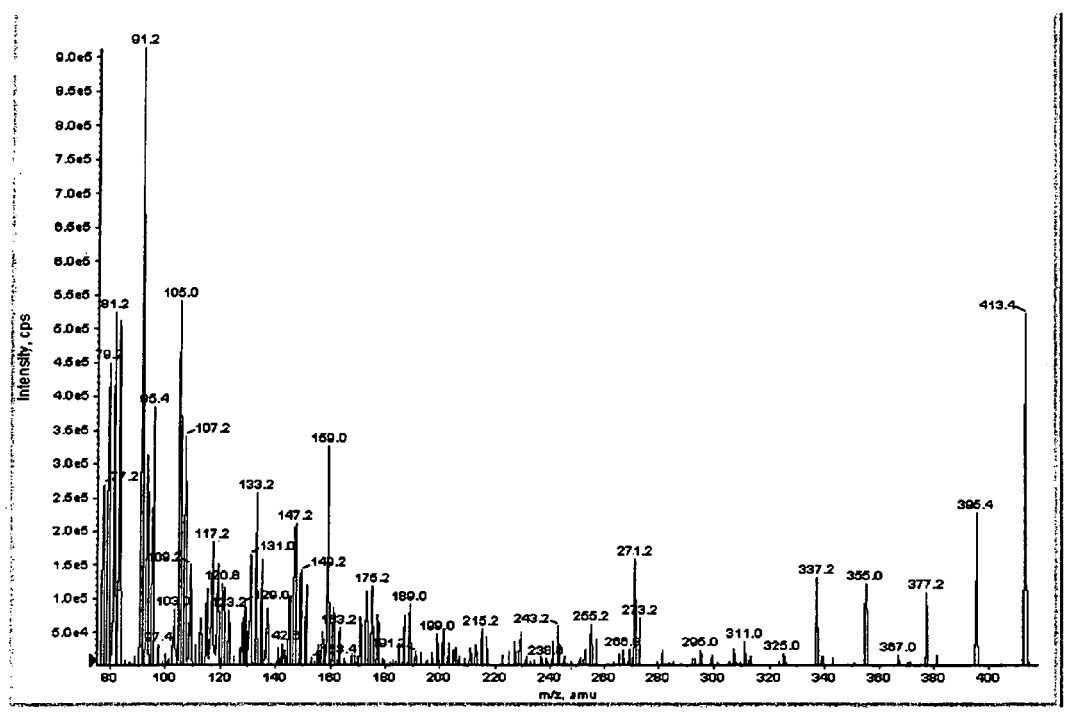
FIG. 2A is a 25OHD2 product ion scan.
Figure 2B:
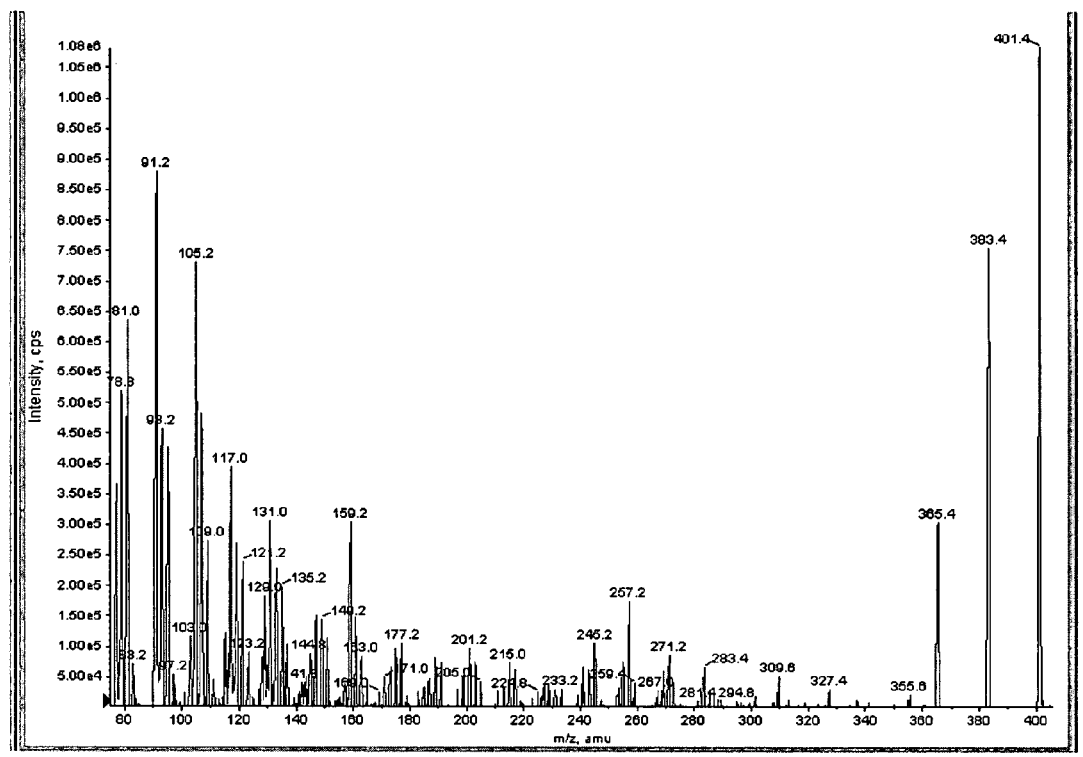
FIG. 2B is a 25OHD3 product ion scan.

The Q1 scan (FIG. 1) and the Q3 scan (FIG. 2) of 25OHD2 (MW 412) and 25OHD3 (MW 400) were obtained by infusing a 5 µg/mL solution at 10 µL/min. The auto tune mode of Analyst software was used to select and optimize ion pairs. Ion pairs were also checked manually and found to be the same. Each compound had an optimum Q1 ion corresponding to [M+H]$^+$ and an optimum Q3 ion corresponding to a $H_2O$ loss. The deuterated internal standard $d_6$-25OHD3 gave a similar ion pair of m/z 407 to 389.

FIG. 3 shows a LC-MS/MS chromatogram of a sample. By collecting data for two minutes, the Cohesive system can collect data on one channel while extracting another sample on the second channel.

Recovery data for each sample type is listed in Table 1. This data demonstrates that each specimen type is acceptable and that the stripped serum used for the standards is an acceptable standard matrix.

TABLE 1

|  | Sensitivity, n = 15 | Low, n = 15 | Medium, n = 15 | High, n = 15 |
| --- | --- | --- | --- | --- |
| 25OHD2 | 4.2 ng/mL | 17 ng/mL | 42 ng/mL | 110 ng/mL |
| CV | 14.0% | 5.0% | 6.5% | 5.7% |
| 25OHD3 | 1.7 ng/mL | 24 ng/mL | 55 ng/mL | 132 ng/mL |
| CV | 12.9% | 8.0% | 7.4% | 5.9% |

The linearity data had a percent observed mean of 109% for 25OHD2 with a range of 93-125%. The 25OHD3 percent observed mean was 103% with a range of 96-118%. Sensitivity was also checked by linearity. One sample for 25OHD2 diluted to 4.1 ng/mL had a percent observed of 96%, and one sample for 25OHD3 diluted to 1.3 ng/mL had a percent observed of 106%.

Precision data is provided in Table 1. 25OHD2 and 25OHD3 had inter-assay precision of <10% in the low, medium and high range. Sensitivity was established at 4 ng/mL for 25OHD2 and 2 ng/mL for 25OHD3 based on an inter-assay CV of <20% on the sensitivity pool.

25OHD2 and 25OHD3 were found to be stable at ambient and refrigerated temperatures for 7 days. Day 7 ambient samples (serum, EDTA plasma, and heparin plasma) had a mean difference of 7.6% from day 0 values with a range of −9.7% to 23.8%. Day 7 refrigerated samples (serum, EDTA plasma and heparin plasma) had a mean difference of 1.6% from day 0 values with a range of −24.2% to 11.9%. Samples were also stable for 3 freeze/thaw cycles. Samples (serum, EDTA plasma and heparin plasma) after 3 freeze/thaw cycles had a mean difference of 0.6% from unfrozen fresh values with a range of −11.5% to 11.5%.

Carry over was assessed by injecting stripped serum supernatants after supernatants of spiked samples (1720-8130 ng/mL) on each system. Three levels of 25OHD2 and 25OHD3 were used with stripped serum run after each level. The amount of detectable 25OHD2 and 25OHD3 in the stripped serum was divided by the concentrations in the spiked samples. 25OHD2 had a carry over of 0.05%-0.14% and 25OHD3 had a carry over of 0.14%-0.24%.

Method comparison correlation data for the four assays tested is in Table 2. Slopes ranged from 1.01-1.03, and r values ranged from 0.87-0.92 for samples that were 25OHD2 negative (only 25OHD3 present). Slopes ranged from 0.48-0.94 and r values ranged from 0.59-0.89 for 25OHD2 positive patients (25OHD2 and 25OHD3 present), indicating the immunoassays used in this comparison underestimate 25OHD2 levels.

TABLE 2

| Assay | Slope | y-intercept | r |
| --- | --- | --- | --- |
| 25OHD2 Negative patients | | | |
| Diasorin RIA | 1.03 | 3.3 | 0.92 |
| Liason | 1.02 | 4.3 | 0.87 |
| Advantage | 1.01 | 3.3 | 0.89 |
| 25OHD2 Positive patients | | | |
| Diasorin RIA | 0.94 | 4.4 | 0.89 |
| Liason | 0.91 | 11.9 | 0.83 |
| Advantage | 0.48 | 10.9 | 0.59 |

Linearity data demonstrate that the stripped serum is an acceptable matrix for standards. Values of the linearity study range from 211 ng/mL in an undiluted sample to as low as 1.3 ng/mL in a diluted sample. This data reinforces the linear range of the standards 0-200 ng/mL.

Carry-over is negligible. Any sample following a sample >1000 ng/mL is repeated to prevent any contamination.

The method comparison data shows good correlation for 25OHD3 samples between all assays. The poor correlation of the Advantage assay in 25OHD2 positive samples indicates the Advantage assay underestimates 25OHD2.

A number of embodiments of the invention have been described. Nevertheless, it will be understood that various modifications may be made without departing from the spirit and scope of the invention.

What is claimed is:

1. A method for simultaneously determining an amount of 25-hydroxyvitamin D2 and an amount of 25-hydroxyvitamin D3 in a single sample, wherein said method comprises using a mass spectrometry technique to detect underivatized 25-hydroxyvitamin D2 and underivatized 25-hydroxyvitamin D3 in said sample, wherein said mass spectrometry technique comprises a LC-MS/MS technique and wherein said LC-MS/MS technique comprises the use of a triple quadrupole instrument in Multiple Reaction Monitoring (MRM), positive-ion mode.

2. The method of claim 1, wherein said LC-MS/MS technique comprises a Q1 scan tuned to select a precursor ion that corresponds to the [M+H+] of 25-hydroxyvitamin D2.

3. The method of claim 1, wherein said sample is a biological sample.

4. The method of claim 3, wherein said biological sample is a mammalian biological sample.

5. The method of claim 4, wherein said mammalian biological sample is a human biological sample.

6. The method of claim 5, wherein said human biological sample is a blood, urine, lachrymal, plasma, serum, or saliva sample.

7. The method of claim 3, wherein said sample is a food sample.

8. The method of claim 1, wherein said LC-MS/MS technique comprises atmospheric pressure chemical ionization.

9. The method of claim 1, wherein said LC-MS/MS technique comprises a Q1 scan tuned to select, independently, precursor ions that correspond to the [M+H+] of 25-hydroxyvitamin D2 and 25-hydroxyvitamin D3.

10. The method of claim 9, wherein said LC-MS/MS technique comprises monitoring MRM precursor-product ion pair transitions having m/z values of 401.4/383.3 for 25-hydroxyvitamin D3 and 413.0/395.3 for 25-hydroxyvitamin D2.

11. The method of claim 1, wherein said method comprises determining said amounts of 25-hydroxyvitamin D2 and 25-hydroxyvitamin D3 using a standard calibration curve.

12. The method of claim 11, further comprising an internal standard selected from the group consisting of a deuterated derivative of 25-hydroxyvitamin D3 and a deuterated derivative of 25-hydroxyvitamin D2.

* * * * *

UNITED STATES PATENT AND TRADEMARK OFFICE
CERTIFICATE OF CORRECTION

PATENT NO. : 7,700,365 B2
APPLICATION NO. : 10/977121
DATED : April 20, 2010
INVENTOR(S) : Ravinder J. Singh It is certified that error appears in the above-identified patent and that said Letters Patent is hereby corrected as shown below:

Title Page, References Cited, Other Publications, Maunsell et al. reference, please delete "Simultancous" and insert --Simultaneous-- therefor;

Title Page, References Cited, Other Publications, Maunsell et al. reference, please delete "Metabolitcs" and insert --Metabolites-- therefor;

Title Page, References Cited, Other Publications, Maunsell et al. reference, please delete "Viramins" and insert --Vitamins-- therefor;

Title Page, References Cited, Other Publications, Yeung et al. reference, please delete "spectromctry" and insert --spectrometry-- therefor;

Title Page, References Cited, Other Publications, Higashi et al. reference, after "D3" please delete "in Human Plasma by Liquid Chromatography-Tandem Mass Spectrometry Employing";

Title Page, References Cited, Other Publications, Vieth reference, please delete "69(5):842:856" and insert --69(5):842-856-- therefor;

Title Page, References Cited, Other Publications, Vogeser et al. reference, please delete "Chromotography" and insert --Chromatography-- therefor;

Column 2, line 4, please delete "$D_2$" and insert --D2-- therefor;

Column 2, line 4, please delete "$D_3$" and insert --D3-- therefor;

Column 2, lines 7-8, please delete "$D_2$" and insert --D2-- therefor;

Column 2, lines 7-8, please delete "$D_3$" and insert --D3-- therefor;

Column 2, line 12, please delete "$D_2$" and insert --D2-- therefor;

Signed and Sealed this

Third Day of August, 2010

David J. Kappos
*Director of the United States Patent and Trademark Office*

CERTIFICATE OF CORRECTION (continued)
U.S. Pat. No. 7,700,365 B2

Column 2, line 12, please delete "$D_3$" and insert --D3-- therefor;

Column 2, line 36, please delete "$D_2$" and insert --D2-- therefor;

Column 2, line 36, please delete "$D_3$" and insert --D3-- therefor;

Column 3, line 15, please delete "[M+H+]" and insert --[M+H$^+$]-- therefor;

Column 9, line 12 (Claim 2), please delete "[M+H+]" and insert --[M+H$^+$]s-- therefor;

Column 10, line 7 (Claim 9), please delete "[M+H+]" and insert --[M+H$^+$]s-- therefor.